(12) United States Patent
Lee

(10) Patent No.: US 9,332,971 B2
(45) Date of Patent: May 10, 2016

(54) BIOPSY SYSTEMS

(75) Inventor: Bernard Lee, Wayland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2707 days.

(21) Appl. No.: 11/117,238

(22) Filed: Apr. 28, 2005

(65) Prior Publication Data

US 2006/0258953 A1     Nov. 16, 2006

(51) Int. Cl.
*A61B 10/02* (2006.01)
*A61B 17/34* (2006.01)
*A61B 10/04* (2006.01)

(52) U.S. Cl.
CPC .......... *A61B 10/0275* (2013.01); *A61B 10/0233* (2013.01); *A61B 17/3421* (2013.01); *A61B 2010/0208* (2013.01); *A61B 2010/045* (2013.01)

(58) Field of Classification Search
CPC .......... A61B 10/0233; A61B 10/0275
USPC .................. 600/564–568; 606/172
See application file for complete search history.

(56) References Cited

U.S. PATENT DOCUMENTS

| | | | |
|---|---|---|---|
| 4,022,191 A | | 5/1977 | Jamshidi et al. |
| 4,958,625 A | | 9/1990 | Bates et al. |
| 5,368,045 A | | 11/1994 | Clement et al. |
| 5,535,755 A | * | 7/1996 | Heske ........................... 600/567 |
| 5,957,888 A | | 9/1999 | Hinchliffe et al. |
| 5,989,196 A | | 11/1999 | Chu et al. |
| 2004/0171989 A1 | * | 9/2004 | Horner et al. ............ 604/164.08 |
| 2005/0165328 A1 | * | 7/2005 | Heske et al. ................... 600/567 |
| 2005/0203439 A1 | * | 9/2005 | Heske et al. ................... 600/566 |
| 2007/0100288 A1 | * | 5/2007 | Bozeman et al. ............. 604/181 |

FOREIGN PATENT DOCUMENTS

| | | |
|---|---|---|
| DE | 202 09 530 U1 | 8/2002 |
| WO | WO 02/77767 A1 * | 9/2003 ............. A61B 10/00 |
| WO | WO 03/077768 A1 * | 9/2003 ............. A61B 10/00 |

OTHER PUBLICATIONS

Heske et al., Device for Intracorporeal Tissue Examination (Translation of DE 20209530 U1), Aug. 29, 2002 original publication in German.*
"Medi•tech® Products for Diagnostic and Interventional Procedures: Biopsy Products", copyright 1994, 4 pages.
"ASAP™ Detachable Biopsy System with Channel Cut™ Needle: Device Photos", retrieved from the Internet on Dec. 29, 2004, 6 pages http://www.bostonscientific.com/med_specialty/deviceDetail.jhtml.

(Continued)

*Primary Examiner* — Lee S Cohen
*Assistant Examiner* — Emily Lloyd
(74) *Attorney, Agent, or Firm* — Bookoff McAndrews, PLLC

(57) ABSTRACT

Biopsy systems, as well as related methods and components, are disclosed. In some embodiments, a biopsy system can include a biopsy gun and a spacer. The biopsy gun can include a housing having a proximal end and a distal end, and a biopsy needle having a proximal end and a distal end. A lumen can extend partially through the housing, and can have a distal end that is defined by the distal end of the housing. A lumen also can extend through the spacer, which can be associated with the distal end of the housing. The biopsy needle can have a first position in which its distal end is disposed within the lumen of the housing or the lumen of the spacer, and a second position in which its distal end is disposed external to the lumen of the housing and the lumen of the spacer.

32 Claims, 13 Drawing Sheets

(56) References Cited

OTHER PUBLICATIONS

"ASAP™ Detachable Biopsy System with Channel Cut™ Needle: Instructions for Use", retrieved from the Internet on Dec. 29, 2004, 1 page http://www.bostonscientific.com/common_templates/singleDetailList.jhtml.

"ASAP™ Detachable Biopsy System with Channel Cut™ Needle (Automated Biopsy Device)", retrieved from the Internet on Dec. 29, 2004, 2 pages http://www.bostonscientific.com/templatedata/imports/collateral/radiology/spec_asap_01_us.pdf.

"Easy Core™ Biopsy System: Device Photos", retrieved from the Internet on Dec. 29, 2004, 15 pages http://www bostonscientific.com/med_specialty/deviceDetail.jhtml.

"Easy Core™ Biopsy System: Instructions for Use", retrieved from the Internet on Dec. 29, 2004, 2 pages http://www.bostonscientific.com/common_templates/singleDetailList.jhtml.

"East Core™ Biopsy System: Breaking the Mold in Device Design", retrieved from the Internet on Dec. 29, 2004, 3 pages http://www.bostonscientific.com/templatedata/imports/collateral/radiololgy/spec_easycore_01_us.pdf.

"Autovac® Full Cut Biopsy", retrieved from the Internet on Dec. 29, 2004, 2 pages http://www.bardnordic.com/main/product.asp.

"Monopty® Disposable Biopsy System", retrieved from the Internet on Dec. 29, 2004, 2 pages http://www.bardnordic.com/main/product.asp.

"Maxcore® Disposable Biopsy Instrument", retrieved from the Internet on Dec. 29, 2004, 2 pages http://www.bardnordic.com/main/product.asp.

"The New Generation of Biopsy Guns", retrieved from the Internet on Dec. 29, 2004, 1 page http://www.amedic.se/guns.html.

"Introducer Sheath", retrieved from the Internet on Dec. 7, 2004, 1 page http://www.amershamhealth.com/medcyclopaedic/medical/volume%2oI.

"PinPoint® Guiding Introducer Needles", retrieved from the Internet on Nov. 24, 2004, 4 pages http://www.bostonscientific.com/med_specialty/deviceDetail.jhtml.

* cited by examiner

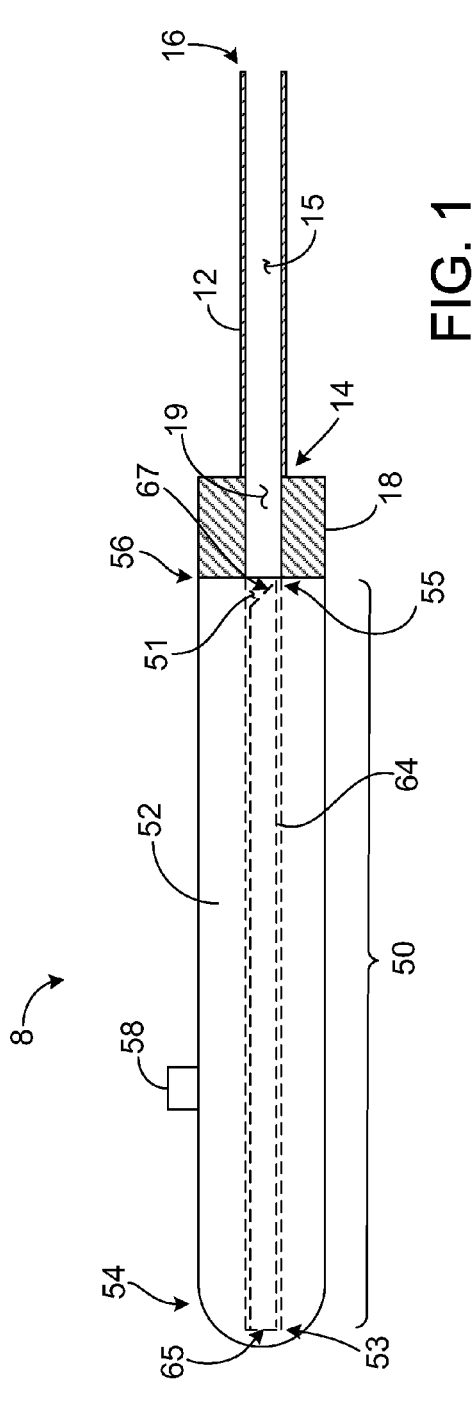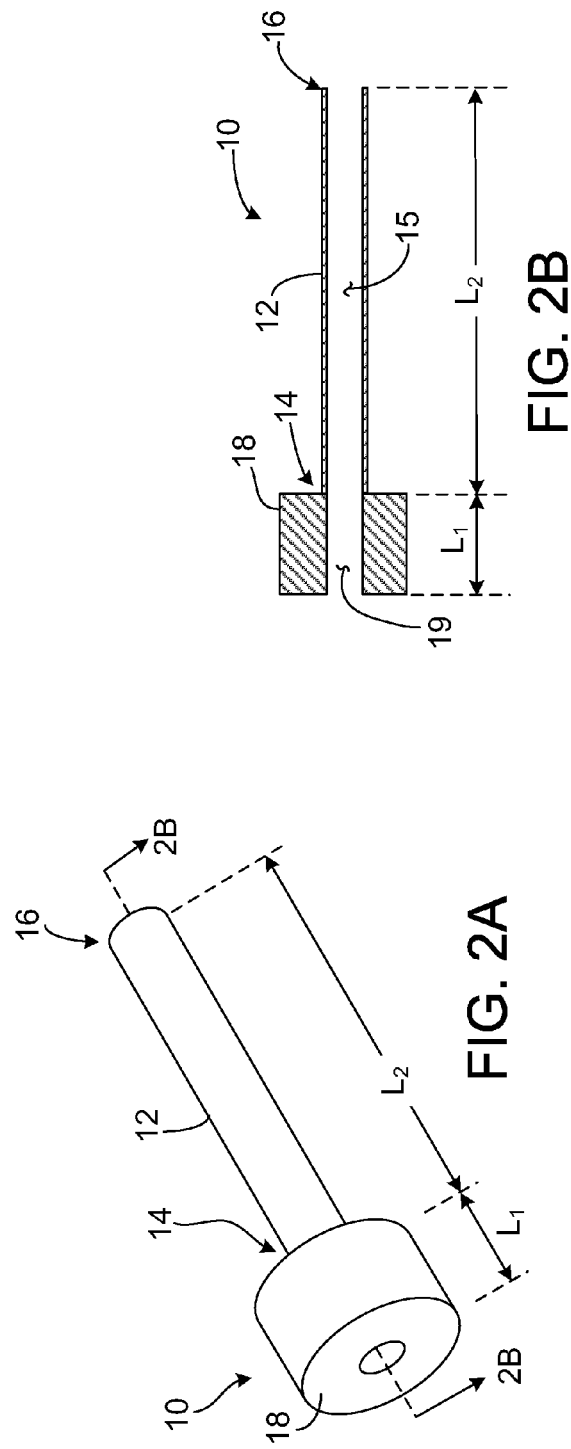

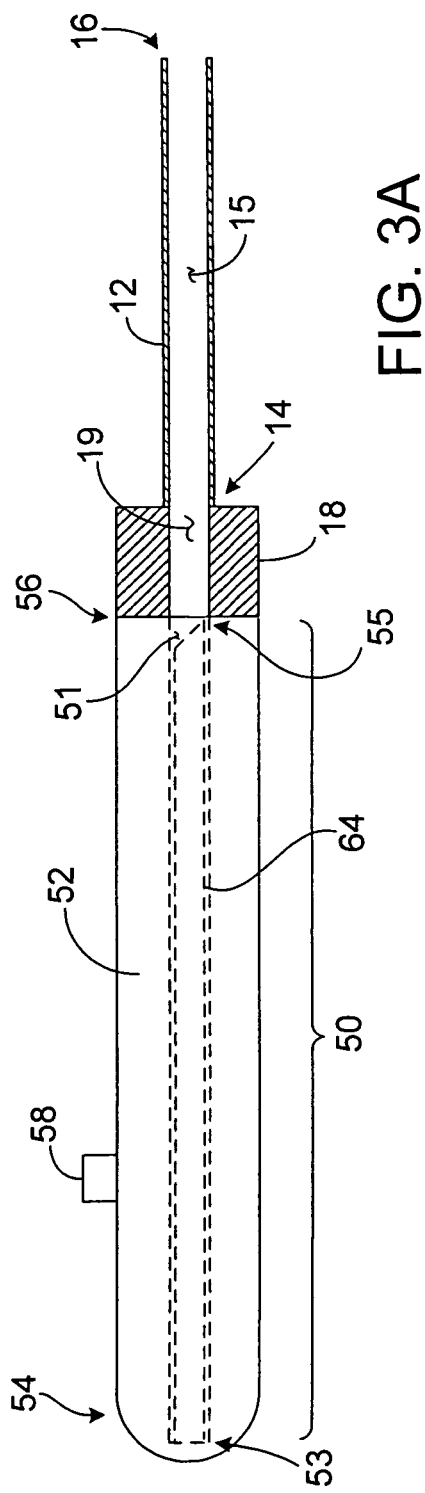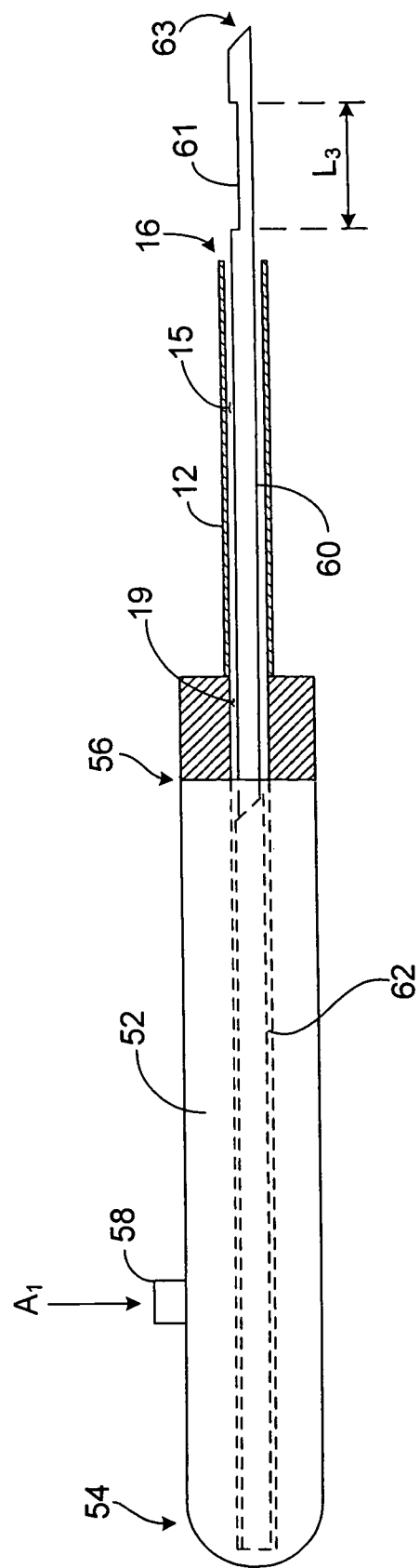

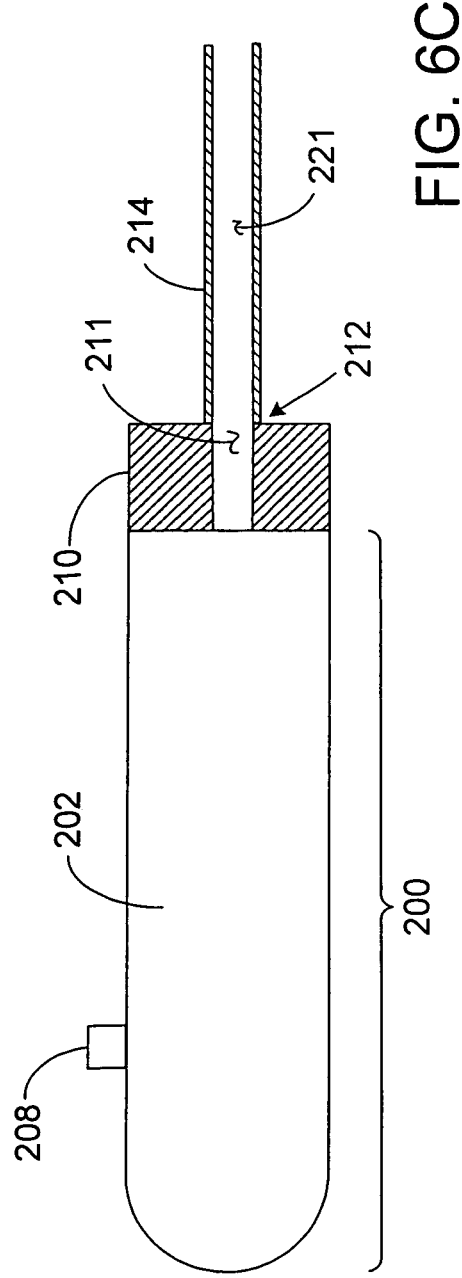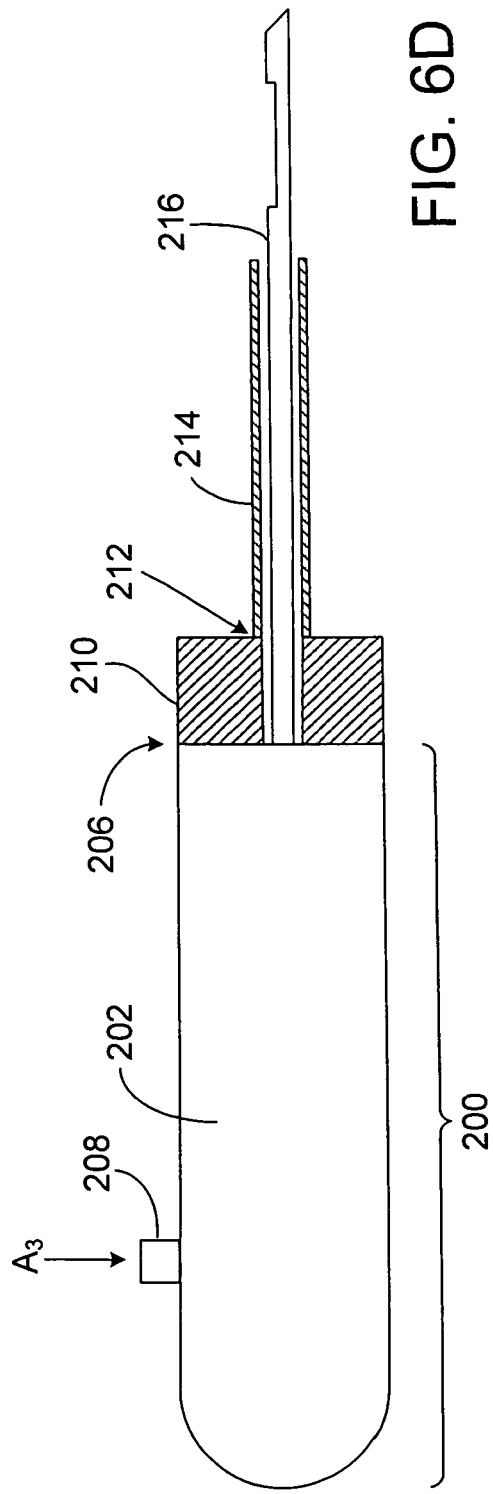

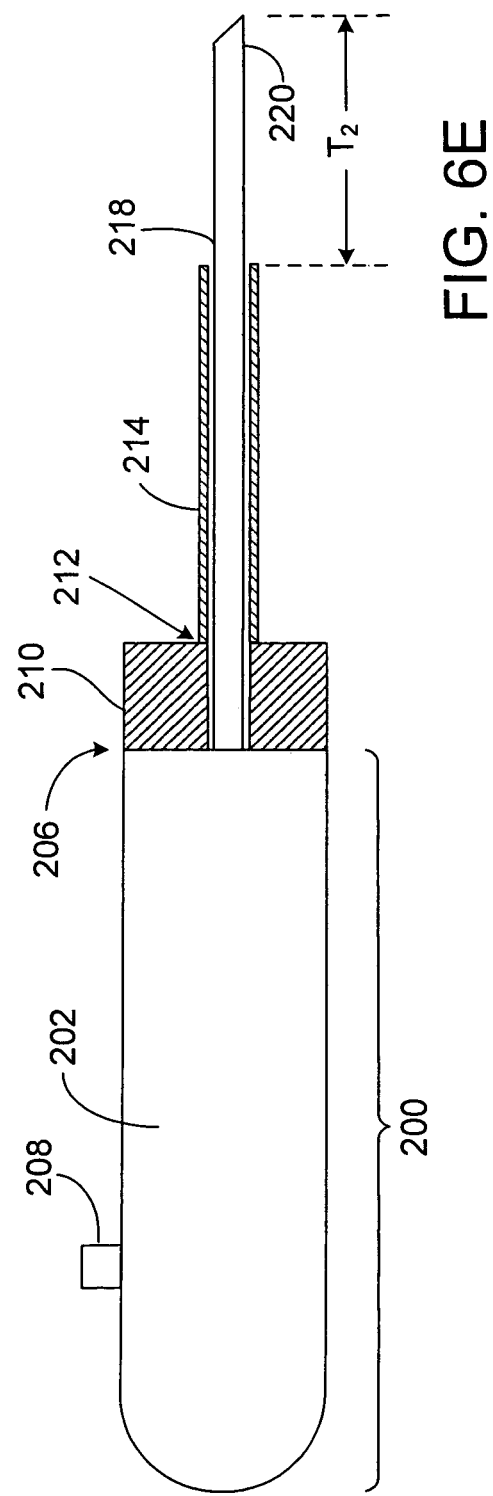

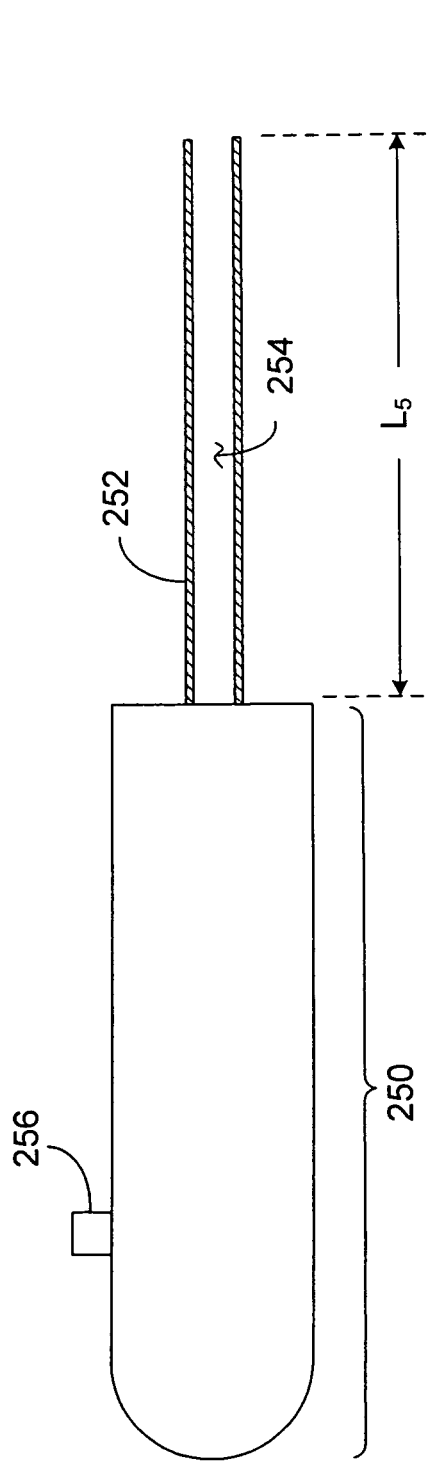
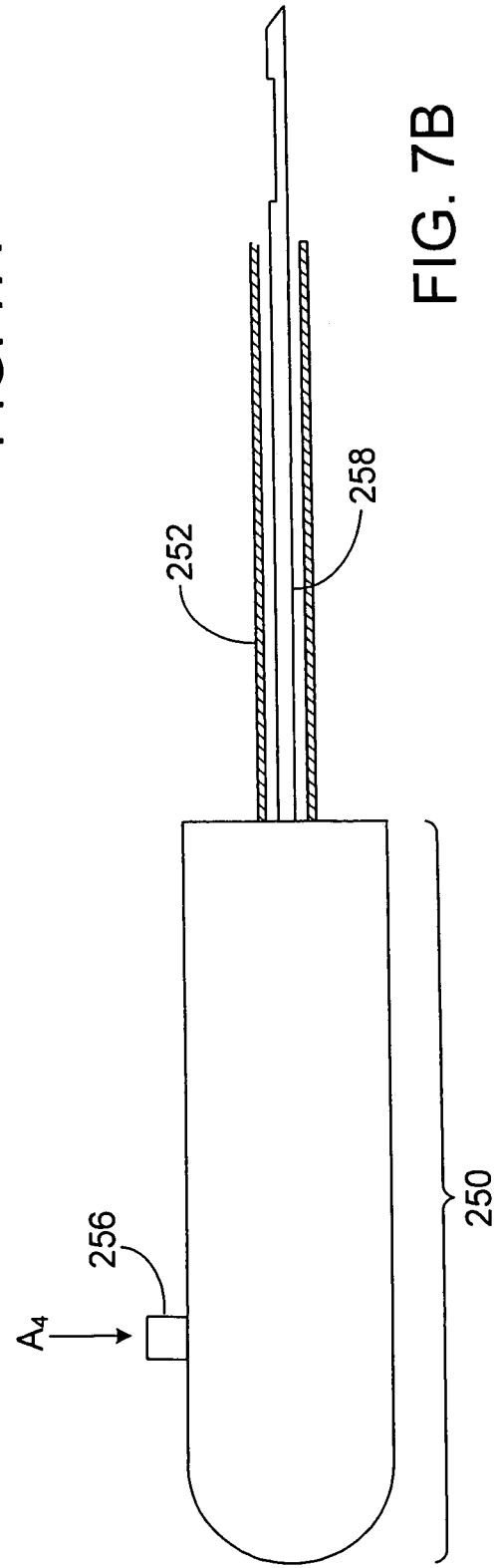

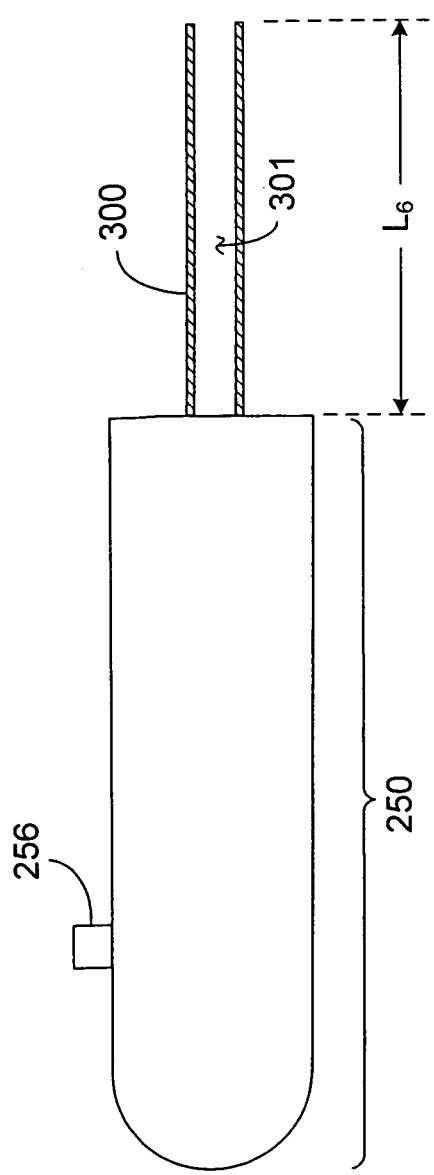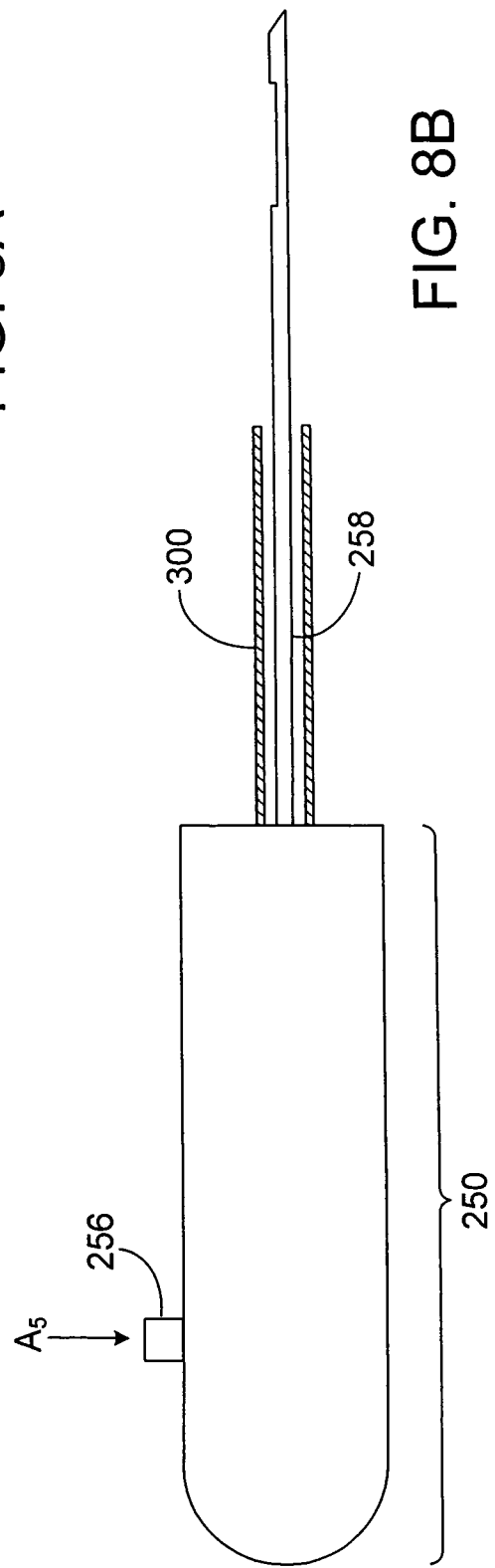

BIOPSY SYSTEMS

TECHNICAL FIELD

The invention relates to biopsy systems, and to related methods and components.

BACKGROUND

Biopsy systems can be used to obtain a tissue specimen from a subject.

SUMMARY

The invention relates to biopsy systems, and to related methods and components.

In one aspect, the invention features a biopsy system including a biopsy gun and a spacer. The biopsy gun includes a housing having a proximal end and a distal end, and a biopsy needle having a proximal end and a distal end. A lumen extends partially through the housing, and has a distal end that is defined by the distal end of the housing. A lumen also extends through the spacer, which is associated with (e.g., connected to and/or integrally formed with) the distal end of the housing. In one position, the distal end of the biopsy needle is disposed within the lumen of the housing or the lumen of the spacer. In another position, the distal end of the biopsy needle is disposed external to the lumen of the housing and the lumen of the spacer. In another aspect, the invention features a method that includes delivering the distal end of an introducer sheath into a body of a subject, and contacting the spacer with the proximal end of the introducer sheath.

In an additional aspect, the invention features an article including an introducer sheath and a spacer. The introducer sheath, which is sized for use with a biopsy gun, has a proximal end, a distal end, and a lumen that extends between the proximal and distal ends. The spacer is associated with (e.g., connected to and/or integrally formed with) the proximal end of the introducer sheath. In a further aspect, the invention features a method that includes delivering the distal end of the introducer sheath into a body of a subject, and contacting the spacer with a biopsy gun including a biopsy needle.

In another aspect, the invention features an article including an introducer sheath and a spacer. The introducer sheath has a proximal end, a distal end, and a lumen extending between the proximal and distal ends. The spacer is associated with (e.g., connected to and/or integrally formed with) the proximal end of the introducer sheath, and is configured to be connected to a biopsy gun. In an additional aspect, the invention features a method that includes delivering the distal end of the introducer sheath into a body of a subject, and contacting the spacer with a biopsy gun including a biopsy needle.

In another aspect, the invention features a medical kit that includes a biopsy gun and at least two introducer sheaths. At least one (e.g., two) of the introducer sheaths can be sized to fit the biopsy gun. The introducer sheaths can have the same length or can have different lengths. In an additional aspect, the invention features a method that includes delivering an end of one of the introducer sheaths into a body of a subject, and contacting the introducer sheath with the biopsy gun.

In a further aspect, the invention features a medical kit that includes a biopsy gun with a housing having a proximal end and a distal end, and at least two spacers. At least one (e.g., two) of the spacers can be adapted to connect to the distal end of the housing. The spacers can have the same length or can have different lengths. In another aspect, the invention features a method that includes delivering the distal end of an introducer sheath into a body of a subject, and contacting one of the spacers with the proximal end of the introducer sheath.

In an additional aspect, the invention features a medical kit that includes an introducer sheath sized for use with a biopsy gun and having a proximal end and a distal end, and at least two spacers. At least one (e.g., two) of the spacers can be adapted to connect to the proximal end of the introducer sheath. The spacers can have the same length or can have different lengths. In a further aspect, the invention features a method that includes delivering the distal end of the introducer sheath into a body of a subject, and contacting one of the spacers with the proximal end of the introducer sheath.

In another aspect, the invention features a medical kit that includes a biopsy gun having a housing with a proximal end and a distal end, a first introducer sheath, and a first spacer. The first introducer sheath has a proximal end and a distal end, and is sized for use with the biopsy gun. The first spacer is adapted to connect to the distal end of the housing of the biopsy gun and to the proximal end of the first introducer sheath. In an additional aspect, the invention features a method that includes delivering the distal end of the first introducer sheath into a body of a subject, connecting the proximal end of the first introducer sheath with the first spacer, and contacting the first spacer with the biopsy gun. In a further aspect, the invention features a method that includes connecting the first spacer with the distal end of the housing of the biopsy gun, delivering the distal end of the first introducer sheath into a body of a subject, and contacting the first spacer with the proximal end of the first introducer sheath.

In an additional aspect, the invention features a medical kit that includes a biopsy gun including a biopsy needle, and an article including an introducer sheath and a spacer. The introducer sheath has a proximal end and a distal end, and the spacer is integrally formed with the proximal end of the introducer sheath. In another aspect, the invention features a method that includes delivering the distal end of the introducer sheath into a body of a subject and contacting the spacer with the biopsy gun.

Embodiments can include one or more of the following features.

The spacer can include a polymer, a metal, and/or a metal alloy. The spacer can have a length of at least about one millimeter, and/or at most about 20 millimeters. The spacer can be in the form of a luer lock. The spacer can be interlocked with, and/or bonded to, the distal end of the housing and/or the proximal end of the introducer sheath. The spacer can have a lumen extending through it. The spacer can be integrally formed with and/or connected to the proximal end of the introducer sheath and/or the distal end of the housing of the biopsy gun.

In some embodiments in which there are at least two spacers (e.g., in a medical kit), the spacers can have the same length or can have different lengths. In certain embodiments, the length of one spacer can be from about 0.1 centimeter to about three centimeters (e.g., from about 0.1 centimeter to about 2.5 centimeters, from about 0.1 centimeter to about 1.5 centimeters), and/or the length of the other spacer can be from about 0.1 centimeter to about three centimeters (e.g., from about 0.5 centimeter to about three centimeters, from about 1.5 centimeters to about three centimeters). In some embodiments in which the spacers have different lengths, the difference between the lengths of the spacers can be at least about 0.1 centimeter (e.g., at least about 0.5 centimeter, at least about one centimeter, at least about two centimeters), and/or at most about 2.5 centimeters (e.g., at most about two centimeters, at most about one centimeter, at most about 0.5 centimeter).

In certain embodiments in which there are at least two spacers (e.g., in a medical kit), the spacers can be adapted to connect to each other.

The biopsy system can include an introducer sheath. The introducer sheath can be sized for use with the biopsy gun, and/or can be configured to be connected to the spacer. In some embodiments, the introducer sheath can have a proximal end and a distal end, and the spacer can be connected to and/or integrally formed with the proximal end of the introducer sheath. In certain embodiments, an introducer sheath can have a length of at least about five centimeters (e.g., at least about 10 centimeters, at least about 15 centimeters, at least about 20 centimeters, at least about 25 centimeters), and/or at most about 30 centimeters (e.g., at most about 25 centimeters, at most about 20 centimeters, at most about 15 centimeters, at most about 10 centimeters). In some embodiments, an introducer sheath can have a length of from about 9.7 centimeters to about 20.2 centimeters.

In some embodiments in which there are at least two introducer sheaths (e.g., in a medical kit), the introducer sheaths can have different lengths. In certain embodiments, the length of one introducer sheath can be from about five centimeters to about 15 centimeters, and/or the length of the other introducer sheath can be from about 15 centimeters to about 30 centimeters. In some embodiments, the difference between the lengths of the introducer sheaths can be at least about five centimeters (e.g., at least about 10 centimeters, at least about 15 centimeters, at least about 20 centimeters), and/or at most about 25 centimeters (e.g., at most about 20 centimeters, at most about 15 centimeters, at most about 10 centimeters).

In certain embodiments in which there are at least two introducer sheaths (e.g., in a medical kit), the introducer sheaths can be adapted to connect to each other.

The biopsy needle can have a length of at least about 50 millimeters (e.g., at least about 75 millimeters, at least about 100 millimeters, at least about 125 millimeters, at least about 150 millimeters, at least about 175 millimeters, at least about 200 millimeters, at least about 225 millimeters), and/or at most about 250 millimeters (e.g., at most about 225 millimeters, at most about 200 millimeters, at most about 175 millimeters, at most about 150 millimeters, at most about 125 millimeters, at most about 100 millimeters, at most about 75 millimeters). For example, in some embodiments, the biopsy needle can have a length of about 100 millimeters, about 120 millimeters, about 130 millimeters, about 150 millimeters, or about 210 millimeters.

In certain embodiments, the biopsy needle can include a stylet having a proximal end and a distal end, and/or a cannula. The stylet can be located within the cannula. A region of the stylet that is adjacent the distal end of the stylet can include a notch. The notch can have a length of at least about five millimeters, and/or at most about 20 millimeters. The distal end of the stylet can be pointed and adapted to penetrate tissue (e.g., in the body of a subject).

The biopsy gun can be a semi-automatic biopsy gun or an automatic biopsy gun. The biopsy gun can be electronically, mechanically, and/or pneumatically activated. In some embodiments, the biopsy gun can include a spring mechanism.

The medical kit can include at least one (e.g., two, three, four, five) introducer sheath. In some embodiments in which the medical kit includes a first introducer sheath, the medical kit can further include a second introducer sheath that has a proximal end and a distal end, and that is sized for use with the biopsy gun. The second introducer sheath can have a different length from the first introducer sheath. The first spacer can be adapted to connect to the proximal end of the second introducer sheath.

In some embodiments, the medical kit can further include a spacer that is configured to connect to at least one of the introducer sheaths. In certain embodiments, the medical kit can further include a spacer that is connected to and/or integrally formed with the biopsy gun and/or at least one of the introducer sheaths. In some embodiments in which the medical kit includes a first spacer, the medical kit can further include a second spacer that is adapted to connect to the distal end of the housing of the biopsy gun, the proximal end of the first introducer sheath, and/or the proximal end of the second introducer sheath.

The method can include delivering the distal end of the introducer sheath into the body of the subject prior to or after contacting the spacer with the biopsy gun. In certain embodiments, the method can include connecting the spacer to the biopsy gun (e.g., to the distal end of a housing of the biopsy gun).

The method can include advancing the biopsy needle through the introducer sheath. Advancing the biopsy needle through the introducer sheath can include advancing the biopsy needle beyond the distal end of the introducer sheath by a distance of at most about 40 millimeters (e.g., at most about 30 millimeters, at most about 20 millimeters). In some embodiments, the biopsy needle can include a stylet, and the method can include advancing the stylet through the introducer sheath. In certain embodiments, the biopsy needle can include both a stylet and a cannula, and the method can include advancing the cannula over the stylet and through the introducer sheath. In some embodiments, the method can include extracting tissue from the body of the subject.

Embodiments can include one or more of the following advantages.

In some embodiments, the biopsy needle can have adjustable throw. The throw of the biopsy needle can be adjusted, for example, by using one or more spacers between the housing of the biopsy gun and the introducer sheath, and/or by varying the size of the introducer sheath. In certain embodiments, a biopsy needle with adjustable throw can be used for multiple different biopsy procedures and/or multiple different subjects. As an example, the throw of the biopsy needle can be adjusted for taking a sample of thyroid tissue, and can thereafter be adjusted for taking a sample of liver tissue and/or kidney tissue. As another example, a biopsy needle with adjustable throw may be appropriate for use on a number of different types of patients. For example, the biopsy needle may be appropriate for use on both a small child and a large adult.

In some embodiments, the throw of the biopsy needle can be adjusted to limit the likelihood of overshooting or undershooting a target site within a body of a subject. For example, in some embodiments, the throw of the biopsy needle can be adjusted so that a relatively large tissue sample can be obtained as a result of the penetration of the target site by the biopsy needle.

In certain embodiments, a biopsy gun can be sold in a kit with multiple spacers (e.g., multiple spacers of different lengths, multiple spacers of the same length) and/or multiple introducer sheaths (e.g., multiple introducer sheaths of different lengths, multiple introducer sheaths of the same length). The kit can, for example, allow a physician to conveniently and efficiently adjust the throw of the biopsy needle of the biopsy gun to suit a particular procedure.

Features and advantages are in the description, drawings, and claims.

DESCRIPTION OF DRAWINGS

FIG. 1 is a side view in partial cross-section of an embodiment of a biopsy system.

FIG. 2A is a perspective view of an embodiment of an article.

FIG. 2B is a side cross-sectional view of the article of FIG. 2A, taken along line 2B-2B.

FIGS. 3A-3C illustrate the use of an embodiment of a biopsy gun with the article of FIGS. 2A and 2B.

FIGS. 6C-6E illustrate the use of the biopsy gun of FIGS. 6A and 6B.

FIGS. 7A-7C illustrate the use of a biopsy gun with an embodiment of an introducer sheath.

FIGS. 8A-8C illustrate the use of the biopsy gun of FIGS. 7A-7C, with another embodiment of an introducer sheath.

DETAILED DESCRIPTION

Figure 3C:
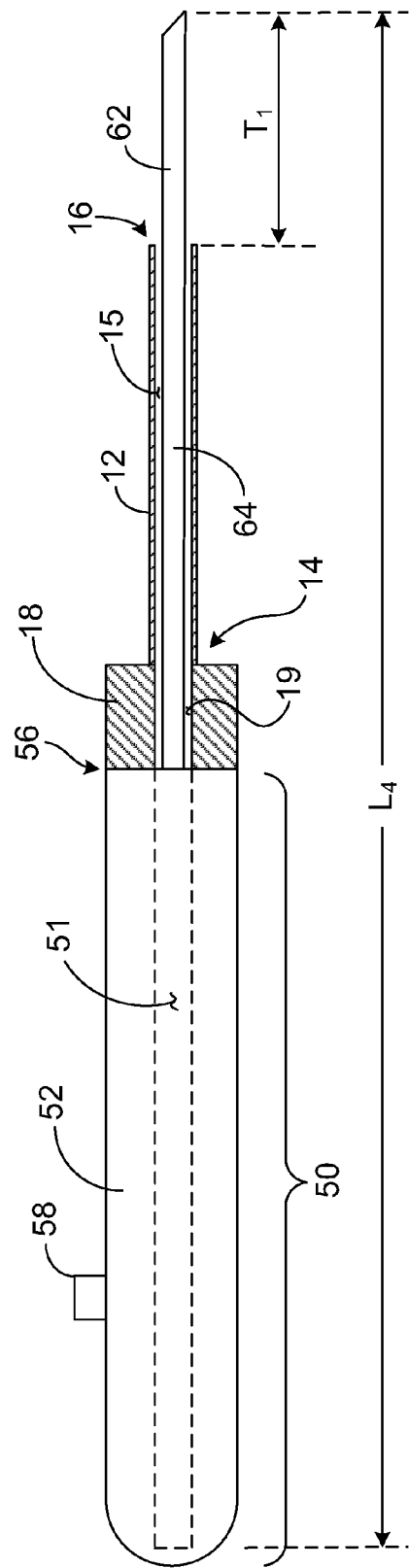

In general, the biopsy systems are designed to include biopsy needles with adjustable throw. The throw of a biopsy needle is the distance by which the biopsy needle extends beyond the distal end of an introducer sheath after the biopsy needle has been deployed through the introducer sheath. In some embodiments, biopsy systems that include biopsy needles with adjustable throw can be used for different types of procedures, and/or on different patients. For example, the throw of a biopsy needle can be adjusted to be relatively short (e.g., less than about 0.5 centimeter, less than about 0.1 centimeter), which can be appropriate when the biopsy needle is used to take a sample of thyroid tissue. Thereafter, the throw of the biopsy needle can be adjusted to be relatively long (e.g., more than about two centimeters, more than about 2.5 centimeters), which can be appropriate when the biopsy needle is used to take a sample of liver tissue and/or kidney tissue. Certain embodiments of the biopsy systems and related components and methods are disclosed below.

In some embodiments, the throw of a biopsy needle can be adjusted using a spacer. For example, FIG. 1 shows a biopsy system 8 that includes a biopsy gun 50, a spacer 18, and an introducer sheath 12. Biopsy gun 50 includes a housing 52 having a proximal end 54 and a distal end 56, a lumen 51 with a proximal end 53 and a distal end 55, and an activation button 58. A biopsy needle 64 is located within lumen 51, and has a proximal end 65 and a distal end 67. Biopsy needle 64 includes a stylet 60 (FIG. 3B) and a cannula 62 (FIG. 3C) surrounding stylet 60. Spacer 18 has a lumen 19, and introducer sheath 12 has a proximal end 14, a distal end 16, and a lumen 15.

Spacer 18 can be connected to either or both of biopsy gun housing 52 and introducer sheath 12. For example, FIGS. 2A and 2B show an article 10 in which spacer 18 is connected to proximal end 14 of introducer sheath 12. Generally, spacer 18 can be connected to introducer sheath 12 using any desired method. Examples of methods include bonding, such as adhesive bonding and/or heat bonding (e.g., using laser heating, using RF heating). For example, in some embodiments, spacer 18 and introducer sheath 12 may be separately formed and then bonded together using an adhesive.

As shown in FIGS. 2A and 2B, spacer 18 has a length $L_1$. In certain embodiments, length $L_1$ can be at least about one millimeter (e.g., at least about three millimeters, at least about five millimeters, at least about seven millimeters, at least about 10 millimeters, at least about 15 millimeters), and/or at most about 20 millimeters (e.g., at most about 15 millimeters, at most about 10 millimeters, at most about seven millimeters, at most about five millimeters, at most about three millimeters).

Spacer 18 can be formed of, for example, a polymer, a metal, a metal alloy, or a combination of these materials. In some embodiments, spacer 18 can be formed of a combination of polymers. Examples of polymers include polyamides (e.g., nylons), copolymers of polyamides (e.g., nylon-polyether copolymers), polyesters (e.g., polyethylene terephthalate (PET) polymers, polybutylene terephthalate (PBT) polymers), copolymers of polyesters, polyetheretherketones (PEEKs), polyurethanes, polyethylenes, polypropylenes, copolymers and ionomers of ethylene, copolymers and ionomers of polypropylene, polystyrenes and copolymers of polystyrenes. Examples of commercially available polymers include the PEBAX® family of polymers (e.g., PEBAX 5533, PEBAX 2533, PEBAX 7033), commercially available from Atofina (Philadelphia, Pa.), the Hytrel family of polymers (e.g., Hytrel 5556, Hytrel 7246, Hytrel 4056), commercially available from E. I. DuPont de Nemours (Wilmington, Del.), and the Arnitel family of polymers (e.g., Arnitel EM630), commercially available from DSM (Erionspilla, Ind.). Examples of metals include platinum, gold, and tantalum. Examples of metal alloys include nitinol, stainless steel (e.g., 303, 304, 316L), and MP35N (a nickel-cobalt-chromium-molybdenum alloy). In some embodiments, spacer 18 can be made of the same material as introducer sheath 12 and/or housing 52 of biopsy gun 50.

As shown in FIGS. 2A and 2B, introducer sheath 12 has a length $L_2$. In some embodiments, length $L_2$ can be at least about five centimeters (e.g., at least about 10 centimeters, at least about 15 centimeters, at least about 20 centimeters, at least about 25 centimeters), and/or at most about 30 centimeters (e.g., at most about 25 centimeters, at most about 20 centimeters, at most about 15 centimeters, at most about 10 centimeters). In certain embodiments, length $L_2$ can be from about nine centimeters to about 20 centimeters.

As FIG. 3A shows, during use of biopsy gun 50, distal end 56 of housing 52 is placed into contact with (e.g., connected to) spacer 18. As shown in FIG. 3B, biopsy gun 50 is activated by pressing activation button 58 downward (in the direction of arrow $A_1$), which causes stylet 60 and then cannula 62 to extend through both lumen 19 of spacer 18 and lumen 15 of introducer sheath 12, as explained in further detail below. Stylet 60 has a pointed distal end 63 and a notch 61 (FIG. 3B), which can serve as a containment space for tissue samples, and which has a length $L_3$. In some embodiments, length $L_3$ can be at least about five millimeters (e.g., at least about 10 millimeters, at least about 15 millimeters), and/or at most about 20 millimeters (e.g., at most about 15 millimeters, at most about 10 millimeters).

As shown in FIG. 3C, biopsy needle 64 has a throw $T_1$ which is equal to the distance by which biopsy needle 64 extends beyond distal end 16 of introducer sheath 12. The presence of spacer 18 causes throw $T_1$ of biopsy needle 64 to be smaller than it would be if spacer 18 were not present. Typically, the presence of spacer 18 can cause throw $T_1$ of biopsy needle 64 to be decreased by the value of length $L_1$ of spacer 18 (FIGS. 2A and 2B), relative to what throw $T_1$ would be if spacer 18 were not used.

In some embodiments, throw $T_1$ can be at least about five millimeters (e.g., at least about 10 millimeters, at least about 12 millimeters, at least about 15 millimeters, at least about 17 millimeters, at least about 20 millimeters, at least about 25 millimeters, at least about 30 millimeters, at least about 35 millimeters), and/or at most about 40 millimeters (e.g., at most about 35 millimeters, at most about 30 millimeters, at most about 25 millimeters, at most about 20 millimeters, at most about 17 millimeters, at most about 15 millimeters, at most about 12 millimeters, at most about 10 millimeters).

The throw of a biopsy needle can be adjusted to be suitable for a particular procedure. In some embodiments, the throw can be adjusted by changing the spacer that is used with the biopsy needle. For example, the throw can be decreased by using a longer spacer, or can be increased by using a shorter spacer. In certain embodiments, the throw can be adjusted by using multiple spacers (e.g., multiple spacers that are adapted to connect to each other). In some embodiments, it may be desirable to adjust the throw of a biopsy needle such that it is relatively short (e.g., less than about 0.5 centimeter, less than about 0.1 centimeter). For example, the throw may be adjusted to be relatively short to limit the likelihood of a biopsy needle extending beyond a target site within the body of a subject. In certain embodiments, it may be desirable to adjust the throw of a biopsy needle such that it is relatively long (e.g., more than about two centimeters, more than about 2.5 centimeters). For example, the throw of a biopsy needle may be adjusted to be relatively long to increase the likelihood of the biopsy needle reaching a distant target site within the body of a subject.

As FIG. 3C shows, biopsy needle 64 has a length $L_4$. In certain embodiments, length $L_4$ can be at least about 50 millimeters (e.g., at least about 100 millimeters, at least about 150 millimeters), and/or at most about 250 millimeters (e.g., at most about 200 millimeters, at most about 150 millimeters, at most about 100 millimeters). For example, length $L_4$ can be about 100 millimeters, about 120 millimeters, about 130 millimeters, about 150 millimeters, or about 210 millimeters.

Figure 4A:
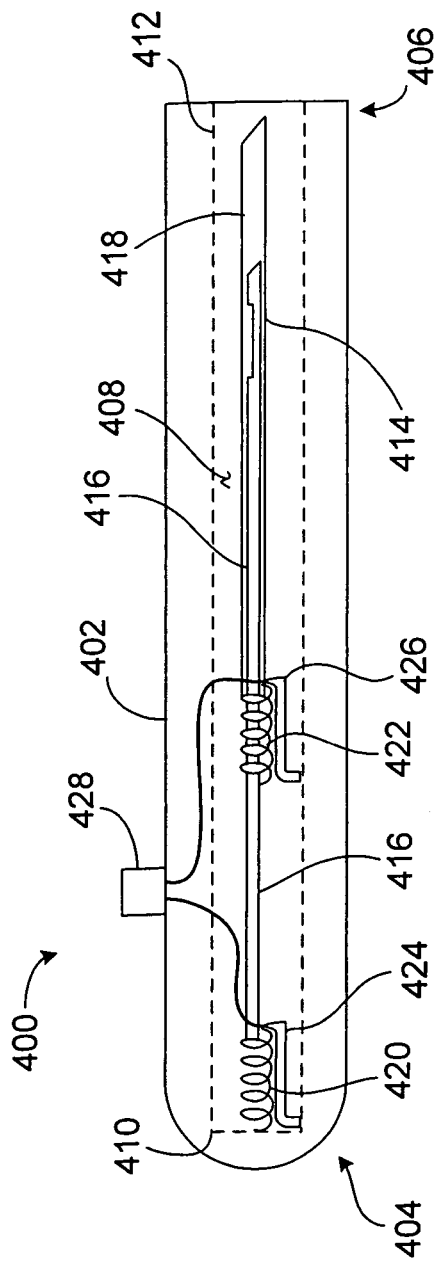
FIG. 4A is a side view in partial cross-section of an embodiment of a biopsy gun.
Figure 4B:
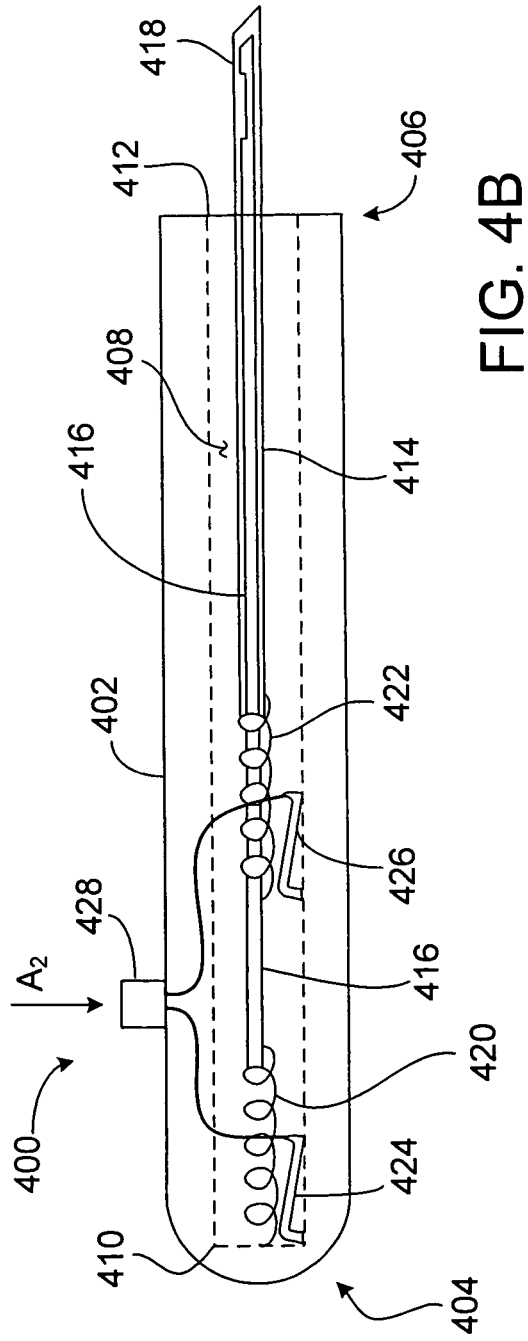
FIG. 4B illustrates the use of the biopsy gun of FIG. 4A.

Biopsy gun 50 can be, for example, an automatic or semi-automatic biopsy gun, and/or can be electronically, mechanically, and/or pneumatically activated. In some embodiments, a biopsy gun such as biopsy gun 50 can be activated by a spring mechanism. For example, FIGS. 4A and 4B show a biopsy gun 400 including a housing 402 having a proximal end 404 and a distal end 406, a lumen 408 having a proximal end 410 and a distal end 412, and an activation button 428. A biopsy needle 414 located within lumen 408, and includes a stylet 416 partially surrounded by a cannula 418. A spring 420 contacts stylet 416 and is held under tension by a lever 424. A spring 422 contacts cannula 418 and is held under tension by a lever 426. As shown in FIG. 4B, when activation button 428 is pressed downward in the direction of arrow $A_2$, activation button 428, which is mechanically connected to levers 424 and 426, causes levers 424 and 426 to press downward, allowing springs 420 and 422 to spring toward distal end 412 of lumen 408, thereby moving stylet 416 and cannula 418 through lumen 408 and past distal end 406 of housing 402.

Biopsy guns (e.g., biopsy guns having spring mechanisms) are described, for example, in Bates et al., U.S. Pat. No. 4,958,625, and Chu et al., U.S. Pat. No. 5,989,196. Examples of commercially available biopsy guns include the Easy Core™ Biopsy System and the ASAP™ Biopsy System, both available from Boston Scientific Corp.

Figure 5:
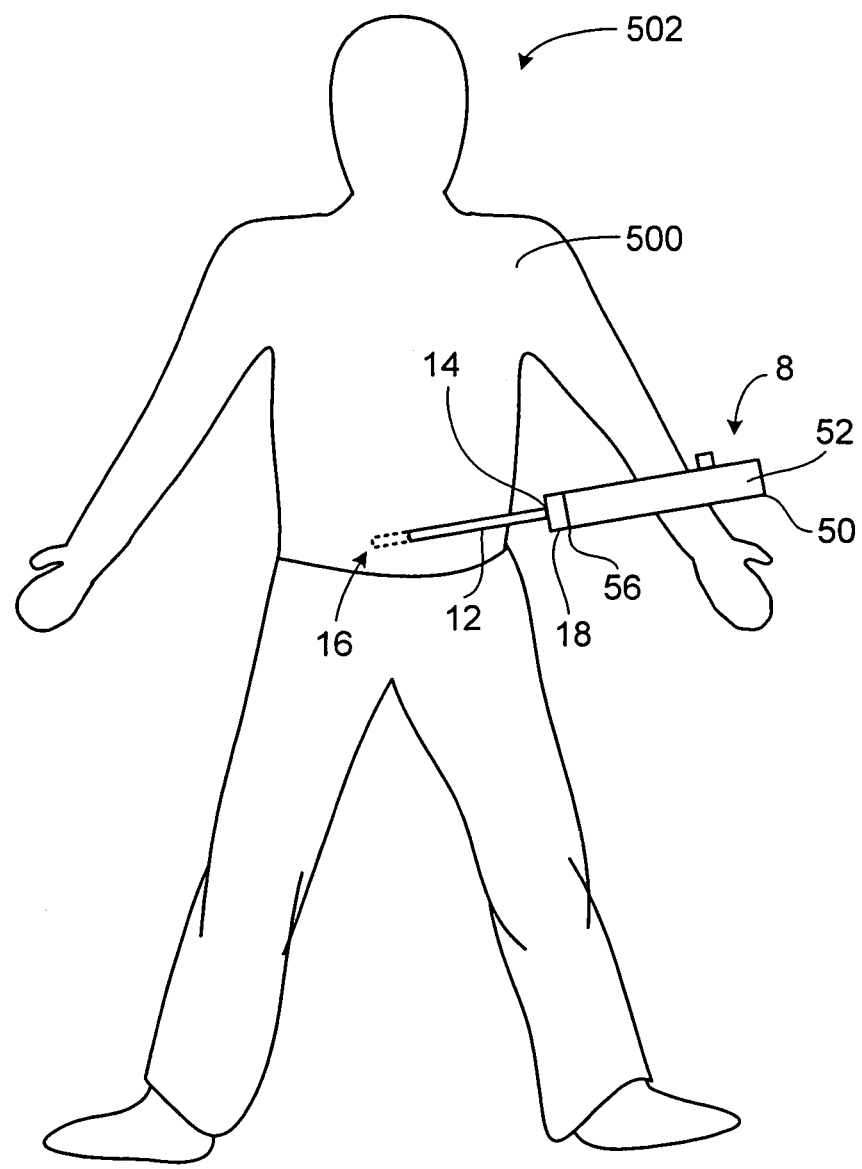
FIG. 5 illustrates the delivery of a portion of a biopsy system into the body of a subject.

FIG. 5 shows biopsy system 8 being used in the body 500 of a subject 502. As shown in FIG. 5, distal end 16 of introducer sheath 12 is inserted into body 500, and spacer 18 contacts both proximal end 14 of introducer sheath 12 and distal end 56 of housing 52 of biopsy gun 50. Biopsy systems such as biopsy system 8 can be used, for example, on soft tissue (e.g., lung, kidney, liver, breast, thyroid), and/or on hard lesions (e.g., hard cancerous lesions) or bone.

While spacers that are connected to introducer sheaths have been shown, in some embodiments, a spacer can be connected to a biopsy gun.

Figure 6A:
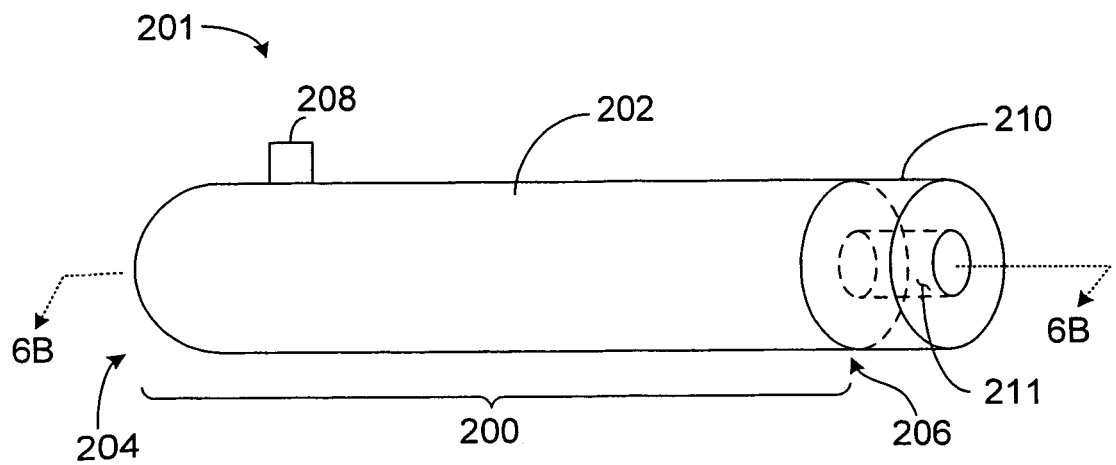
FIG. 6A is a side perspective view of an embodiment of a biopsy gun.
Figure 6B:
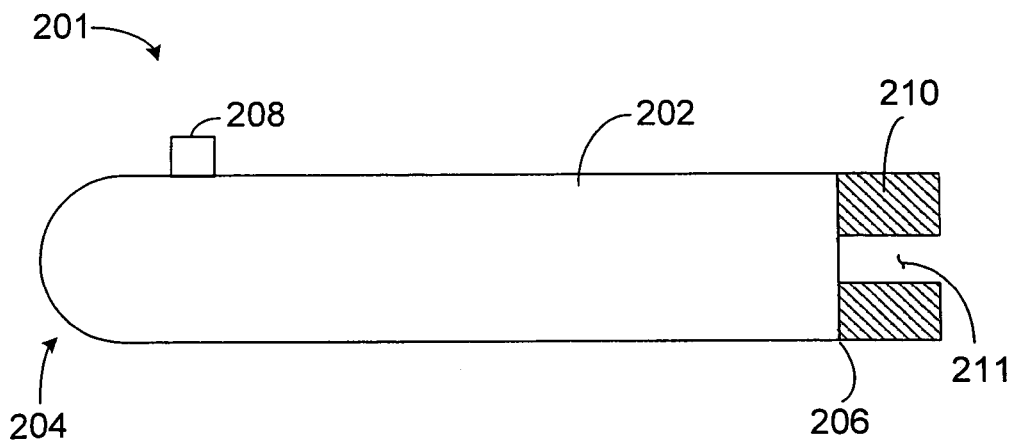
FIG. 6B is a side view in partial cross-section of the biopsy gun of FIG. 6A, taken along line 6B-6B.

For example, FIGS. 6A and 6B show a biopsy system 201 including a biopsy gun 200 and a spacer 210 with a lumen 211. Biopsy gun 200 has a housing 202 with a proximal end 204 and a distal end 206. Biopsy gun 200 also includes a biopsy needle 220 (FIG. 6E) including a stylet 216 (FIG. 6D) and a cannula 218 (FIG. 6E). Biopsy gun 200 further includes an activation button 208. Spacer 210 is connected to distal end 206 of housing 202 using, for example, any of the methods described above with reference to the connection of spacer 18 to introducer sheath 12. Spacer 210 can be formed of, for example, any of the materials described above with reference to spacer 18. In some embodiments, spacer 210 can be formed of the same material as housing 202 of biopsy gun 200.

As shown in FIG. 6C, prior to and/or during use of biopsy gun 200, spacer 210 contacts (e.g., is connected to) the proximal end 212 of an introducer sheath 214 having a lumen 221. As shown in FIGS. 6D and 6E, biopsy gun 200 is then activated by pressing down on activation button 208 in the direction of arrow $A_3$, thereby causing stylet 216 and cannula 218 to extend through lumen 221 of introducer sheath 214.

Biopsy needle 220 has a throw $T_2$ (FIG. 6E). In some embodiments, throw $T_2$ can be at least about five millimeters (e.g., at least about 10 millimeters, at least about 12 millimeters, at least about 15 millimeters, at least about 17 millimeters, at least about 20 millimeters), and/or at most about 21 millimeters (e.g., at most about 20 millimeters, at most about 17 millimeters, at most about 15 millimeters, at most about 12 millimeters, at most about 10 millimeters).

In some embodiments, a biopsy gun can be a component of a medical kit that includes multiple (e.g., two, three, four, five) spacers. The medical kit can include spacers of the same length and/or spacers of different lengths. In certain embodiments, the spacers may be adapted to connect to each other. In some embodiments, the medical kit can include an introducer sheath, and the spacers can be adapted to connect to the biopsy gun and/or the introducer sheath.

In certain embodiments, a medical kit can include a spacer having a length of from about 0.1 centimeter to about three centimeters (e.g., from about 0.1 centimeter to about 2.5 centimeters, from about 0.1 centimeter to about 1.5 centimeters), and another spacer having a length of from about 0.1 centimeter to about three centimeters (e.g., from about 0.5 centimeter to about three centimeters, from about 1.5 centimeters to about three centimeters). In some embodiments in which spacers in a medical kit have different lengths, the difference between the length of one spacer in the medical kit and the length of another spacer in the medical kit can be at least about 0.1 centimeter (e.g., at least about 0.5 centimeter, at least about one centimeter, at least about two centimeters), and/or at most about 2.5 centimeters (e.g., at most about two centimeters, at most about one centimeter, at most about 0.5 centimeter). In certain embodiments in which spacers in a medical kit have the same length, the spacers can each have a length of from about 0.1 centimeter to about two centimeters (e.g., from about 0.1 centimeter to about one centimeters, about 0.5 centimeter).

While the adjustment of the throw of a biopsy needle using a spacer has been described, in certain embodiments, the throw of a biopsy needle can be adjusted using introducer sheaths of different lengths. For example, FIGS. 7A-7C and 8A-8C illustrate the use of introducer sheaths of different lengths with the same biopsy needle.

Figure 7C:
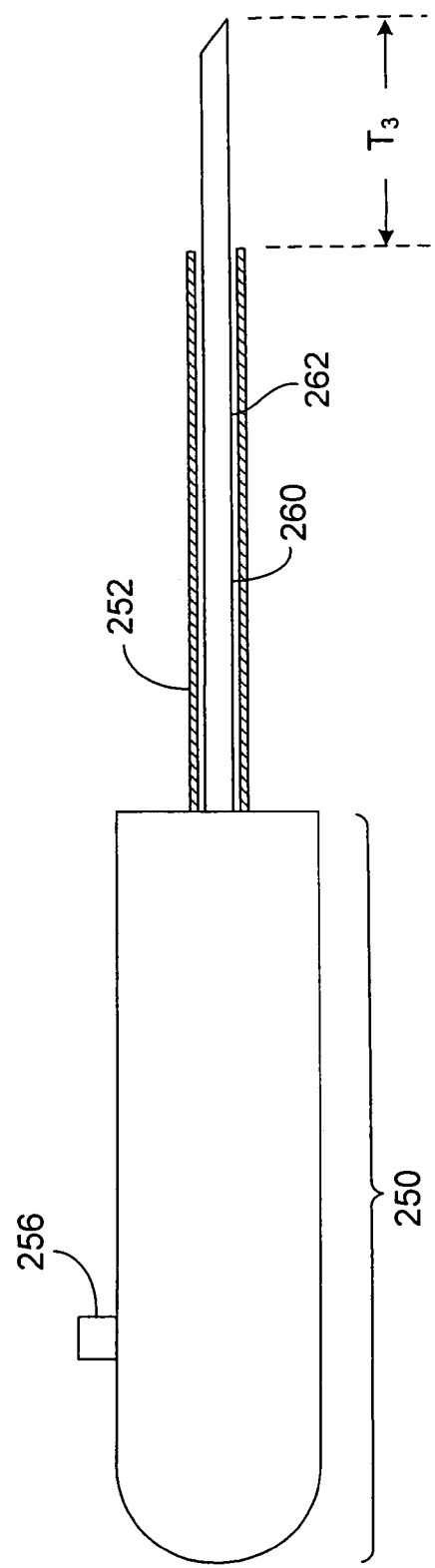

FIGS. 7A-7C illustrate the use of a biopsy gun 250 with an introducer sheath 252 having a lumen 254 and a length $L_5$. In some embodiments, length $L_5$ can be at least about 15 centimeters (e.g., at least about 20 centimeters, at least about 25 centimeters), and/or at most about 30 centimeters (e.g., at most about 25 centimeters, at most about 20 centimeters).

Biopsy gun 250 includes a biopsy needle 262 (FIG. 7C) with a stylet 258 (FIG. 7B) and a cannula 260 (FIG. 7C). When biopsy gun 250 is activated by pressing down on its activation button 256 in the direction of arrow $A_4$ (FIG. 7B), stylet 258 and cannula 260 extend through lumen 254 of introducer sheath 252. Biopsy needle 262 has a throw $T_3$ (FIG. 7C). In certain embodiments, throw $T_3$ can be at least about five millimeters (e.g., at least about 10 millimeters, at least about 12 millimeters, at least about 15 millimeters, at least about 17 millimeters, at least about 20 millimeters), and/or at most about 21 millimeters (e.g., at most about 20 millimeters, at most about 17 millimeters, at most about 15 millimeters, at most about 12 millimeters, at most about 10 millimeters).

Figure 8C:
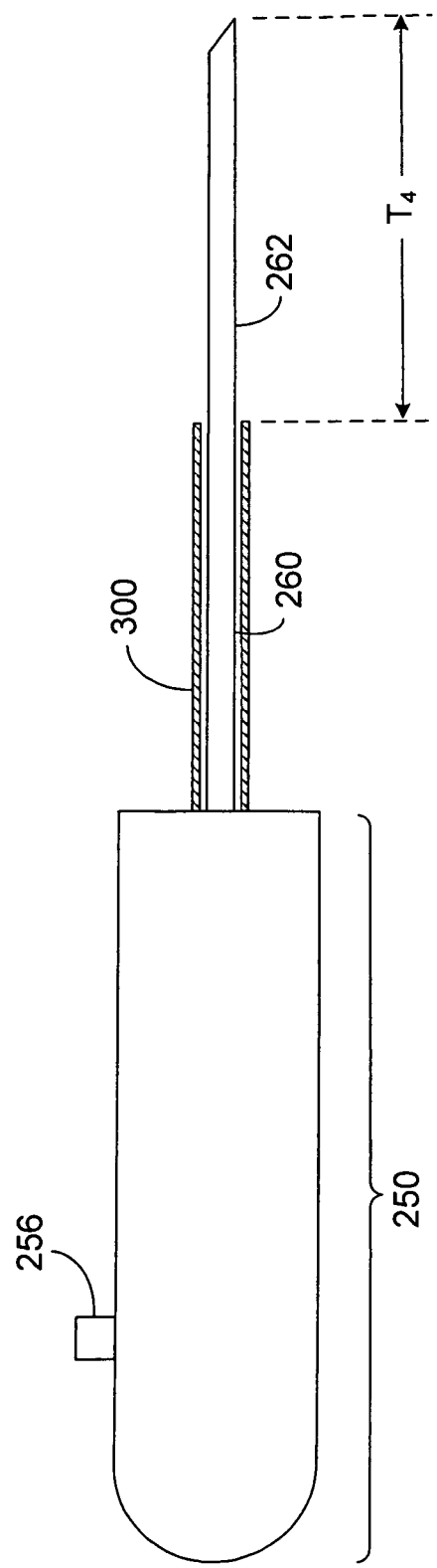

FIGS. 8A-8C also show the use of biopsy gun 250; however, FIGS. 8A-8C show the use of biopsy gun 250 with an introducer sheath 300 that is shorter than introducer sheath 252 of FIGS. 7A-7C. As shown in FIG. 8A, introducer sheath 300 has a lumen 301 and a length $L_6$. In some embodiments, length $L_6$ can be at least about five centimeters (e.g., at least about 10 centimeters), and/or at most about 15 centimeters (e.g., at most about 10 centimeters).

When biopsy gun 250 is activated by pressing down on activation button 256 in the direction of arrow $A_5$ (FIG. 8B), stylet 258 and cannula 260 extend through lumen 301 of introducer sheath 300. Biopsy needle 262 has a throw $T_4$ (FIG. 8C). In some embodiments, throw $T_4$ can be at least about 10 millimeters (e.g., at least about 12 millimeters, at least about 15 millimeters, at least about 17 millimeters, at least about 20 millimeters, at least about 25 millimeters, at least about 30 millimeters), and/or at most about 35 millimeters (e.g., at most about 30 millimeters, at most about 25 millimeters, at most about 20 millimeters, at most about 17 millimeters, at most about 15 millimeters, at most about 12 millimeters).

In certain embodiments, the difference between throw $T_3$ and throw $T_4$ can be at least about one millimeter (e.g., at least about three millimeters, at least about five millimeters, at least about 10 millimeters, at least about 15 millimeters, at least about 20 millimeters, at least about 25 millimeters), and/or at most about 30 millimeters (e.g., at most about 25 millimeters, at most about 20 millimeters, at most about 15 millimeters, at most about 10 millimeters, at most about five millimeters, at most about three millimeters).

In some embodiments, a biopsy gun such as biopsy gun 250 can be a component of a medical kit that also includes multiple (e.g., two, three, four, five) introducer sheaths of different lengths, such as introducer sheaths 252 and 300. For example, the medical kit can include an introducer sheath having a length of from about five centimeters to about 15 centimeters, and another introducer sheath having a length of from about 15 centimeters to about 30 centimeters. In certain embodiments, the difference between the length of one introducer sheath in the medical kit and the length of another introducer sheath in the medical kit can be at least about five centimeters (e.g., at least about 10 centimeters, at least about 15 centimeters, at least about 20 centimeters), and/or at most about 25 centimeters (e.g., at most about 20 centimeters, at most about 15 centimeters, at most about 10 centimeters).

Introducer sheaths such as introducer sheaths 252 and 300 can be formed, for example, of one or more polymers. Examples of polymers include silicones, thermoplastic polymers, thermoset polymers, polyetheretherketones (PEEKs), and high density polyethylene (HDPE). Examples of commercially available polymers include the PEBAX® family of polymers, the Hytrel family of polymers, and the Arnitel family of polymers.

While certain embodiments have been described, the invention is not so limited.

As an example, while biopsy guns and introducer sheaths that are connected to a single spacer have been shown, in some embodiments, multiple spacers (e.g., two, three, four, five) can be used with a biopsy gun and/or an introducer sheath. The spacers may have the same length or may have different lengths. As an example, in some embodiments, a spacer can be connected to the distal end of a biopsy gun, and another spacer can be connected to the proximal end of an introducer sheath that also is used with the biopsy gun. As another example, in certain embodiments, a spacer can be connected to another spacer and to the distal end of a biopsy gun.

Figure 9:
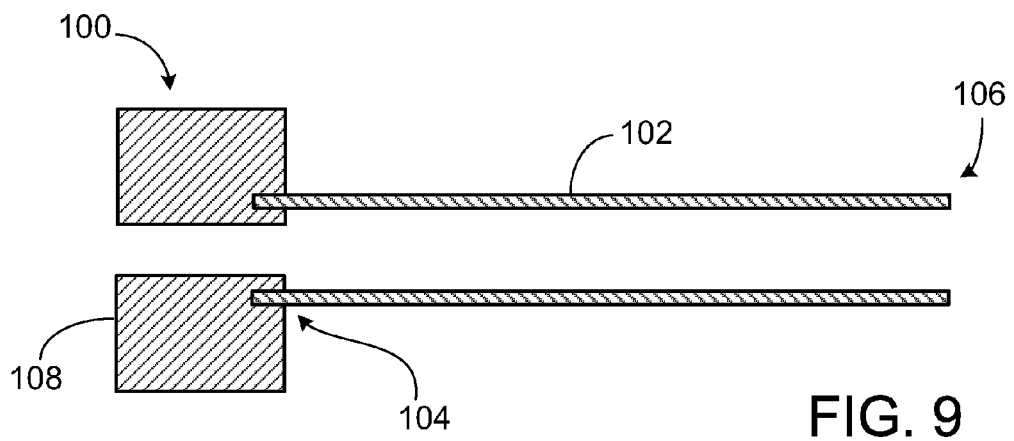
FIG. 9 is a side cross-sectional view of an embodiment of an article.

As another example, in certain embodiments, a spacer can interlock with an introducer sheath (e.g., the spacer can be in the form of a luer lock) and/or a biopsy gun housing. For example, FIG. 9 shows an article 100 that includes an introducer sheath 102 having a proximal end 104 and a distal end 106, and a spacer 108 interlocked with proximal end 104.

Figure 10:
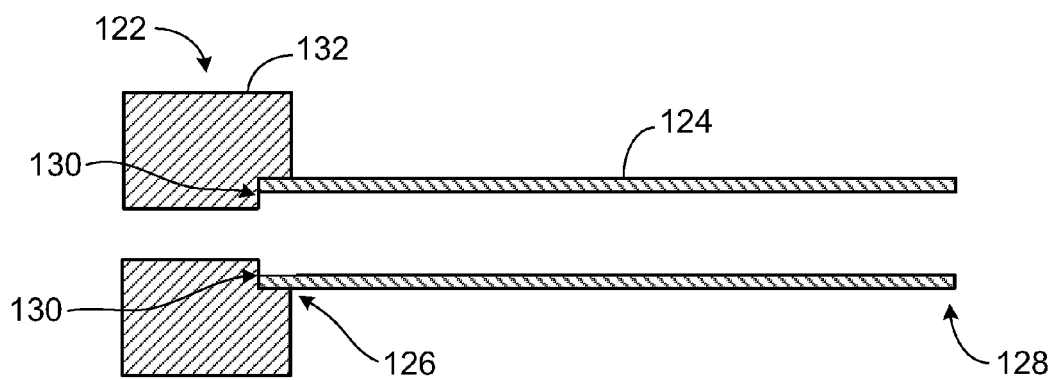
FIG. 10 is a side cross-sectional view of an embodiment of an article.

As a further example, in some embodiments, a spacer can include a ledge that accommodates an introducer sheath or an end of a biopsy gun housing. For example, FIG. 10 shows an article 122 that includes an introducer sheath 124 having a proximal end 126 and a distal end 128. At proximal end 126, introducer sheath 124 contacts a ledge 130 of a spacer 132.

Figure 11:
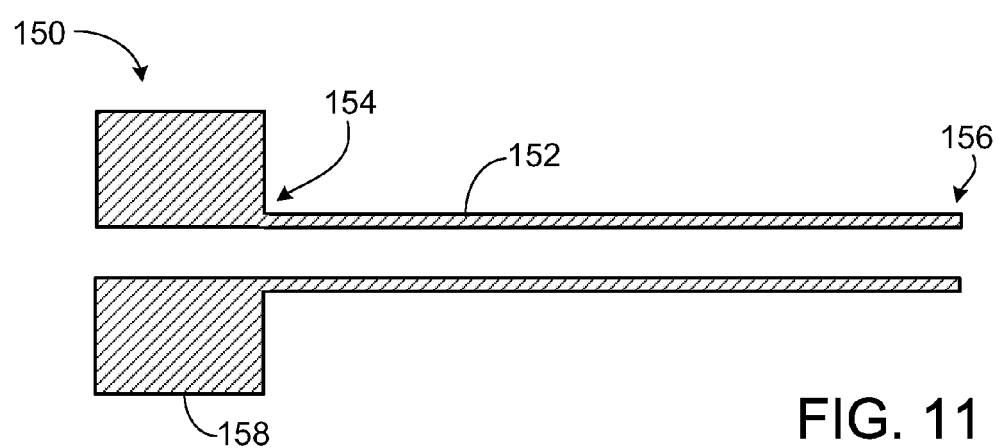
FIG. 11 is a side cross-sectional view of an embodiment of an article.

As an additional example, in some embodiments, a spacer can be integrally formed (e.g., molded, extruded) with an introducer sheath and/or a biopsy gun housing. For example, FIG. 11 shows an article 150 that includes an introducer sheath 152 having a proximal end 154 and a distal end 156, and a spacer 158 integrally formed with introducer sheath 152 at its proximal end 154.

As a further example, in certain embodiments, a medical kit can include a biopsy gun, multiple spacers (e.g., multiple spacers of different lengths, multiple spacers of the same length), and multiple introducer sheaths of different lengths. In some embodiments, the spacers can be adapted to connect to the biopsy gun (e.g., to the distal end of the housing of the biopsy gun), and/or to at least one (e.g., all) of the introducer sheaths (e.g., to the proximal end of one of the introducer sheaths).

As another example, while the adjustment of the throw of a biopsy needle by using multiple spacers has been described, in some embodiments, multiple introducer sheaths can be used to adjust the throw of a biopsy needle. In certain embodiments, the introducer sheaths may be adapted to connect to each other.

As a further example, while medical kits including multiple introducer sheaths of different lengths have been described, in some embodiments, a medical kit can include multiple (e.g., two, three, four, five) introducer sheaths of the same length.

As another example, in some embodiments, a spacer, a biopsy gun, and/or an introducer sheath can have the same color (e.g., blue, green, red), and/or can be provided together in a kit. In certain embodiments, the color of a spacer can provide a signal (e.g., to a physician) as to which biopsy gun(s) and/or introducer sheath(s) are adapted to be connected to the spacer.

Other embodiments are in the claims.

What is claimed is:

1. A biopsy system, comprising:
a housing having a proximal end, a distal end, and a lumen extending partially through the housing, the distal end of the housing defining a distal end of the lumen;
a biopsy needle having a proximal end and a distal end;
a one-piece spacer having a proximal end and a distal end, the proximal end of the spacer being associated with the distal end of the housing, and the spacer having a lumen extending therethrough between the proximal and distal ends of the spacer; and
an introducer sheath having a proximal end and a distal end, and the introducer sheath having a lumen extending therethrough between the proximal and distal ends of the introducer sheath,
wherein the biopsy needle has a first position in which the distal end of the biopsy needle is disposed within the lumen of the housing or the lumen of the spacer, and a second position in which the distal end of the biopsy needle is disposed external to the lumen of the housing and the lumen of the spacer, and
wherein the lumen of the spacer is contiguous with the lumen of the introducer sheath, and a first diameter of the lumen of the spacer is less than a diameter of the lumen of the introducer sheath.

2. The biopsy system of claim 1, wherein the spacer comprises a polymer, a metal, a metal alloy, or a combination thereof.

3. The biopsy system of claim 1, wherein the spacer has a length from about one millimeter to about three centimeters.

4. The biopsy system of claim 1, wherein the spacer is connected to the distal end of the housing.

5. The biopsy system of claim 4, wherein the spacer is interlocked with the distal end of the housing.

6. The biopsy system of claim 4, wherein the spacer is bonded to the distal end of the housing.

7. The biopsy system of claim 1, wherein the biopsy needle has a length of at least about 50 millimeters and at most about 250 millimeters.

8. The biopsy system of claim 1, wherein the biopsy needle comprises a stylet having a proximal end and a distal end.

9. The biopsy system of claim 8, wherein a region of the stylet that is adjacent the distal end of the stylet includes a notch.

10. The biopsy system of claim 1, wherein a distance between the proximal end of the spacer and the distal end of the spacer is greater than a distance between the proximal end of the spacer and the proximal end of the introducer sheath.

11. The biopsy system of claim 1, wherein the lumen of the spacer includes a first portion with the first diameter and a second portion distal to the first portion with a second diameter, wherein the second diameter is greater than the first diameter.

12. The biopsy system of claim 11, wherein the second diameter is greater than an outer diameter of the introducer sheath.

13. The biopsy system of claim 11, wherein the spacer includes a distally-facing ledge at a distalmost end of the first portion, and the introducer sheath contacts the ledge.

14. A method, comprising:
using the biopsy system of claim 1 by delivering the distal end of the introducer sheath into a body of a subject.

15. The method of claim 14, further comprising advancing the biopsy needle through the introducer sheath.

16. The method of claim 15, wherein advancing the biopsy needle through the introducer sheath comprises advancing the biopsy needle beyond the distal end of the introducer sheath by a distance of at most about 40 millimeters.

17. The method of claim 14, further comprising extracting tissue from the body of the subject with the biopsy needle.

18. A biopsy system, comprising:
a biopsy gun having a lumen and a biopsy needle disposed within the lumen of the biopsy gun;
an introducer sheath having a proximal end, a distal end, and a lumen extending between the proximal and distal ends; and
a spacer associated with the proximal end of the introducer sheath,
wherein:
the spacer has a proximal end, a distal end and a lumen having a constant diameter from the proximal end of the spacer to the distal end of the spacer;
the lumen of the spacer is contiguous with the lumen of the introducer sheath; the diameter of the lumen of the spacer is less than a diameter of the lumen of the introducer sheath; and the lumen of the spacer and the lumen of the introducer sheath are configured to accept the biopsy needle.

19. The biopsy system of claim 18, wherein the spacer comprises a polymer, a metal, a metal alloy, or a combination thereof.

20. The biopsy system of claim 18, wherein the spacer is interlocked with the proximal end of the introducer sheath.

21. The biopsy system of claim 18, wherein the spacer is bonded to the proximal end of the introducer sheath.

22. The biopsy system of claim 18, wherein the spacer has a length of at least about one millimeter.

23. The biopsy system of claim 18, wherein the spacer has a length of at most about three centimeters.

24. A method, comprising:
using the biopsy system of claim 18 by delivering the distal end of the introducer sheath into a body of a subject.

25. The method of claim 24, further comprising advancing the biopsy needle through the introducer sheath.

26. The method of claim 25, wherein advancing the biopsy needle through the introducer sheath comprises advancing the biopsy needle beyond the distal end of the introducer sheath by a distance of at most about 40 millimeters.

27. A biopsy system, comprising:
a biopsy gun having a lumen and a biopsy needle disposed within the lumen of the biopsy gun;
an introducer sheath having a proximal end, a distal end, and a lumen extending between the proximal and distal ends; and
a spacer associated with the proximal end of the introducer sheath,
wherein:
the spacer has a proximal end, a distal end and a lumen extending therebetween;

a distance between the proximal and distal ends of the spacer is greater than a distance between the proximal end of the spacer and the proximal end of the introducer sheath;

the spacer is configured to be connected to the biopsy gun;

the lumen of the spacer is contiguous with the lumen of the introducer sheath;

a first diameter of the lumen of the spacer is less than a diameter of the lumen of the introducer sheath, wherein the lumen of the spacer includes a first portion with the first diameter and a second portion distal to the first portion with a second diameter, wherein the second diameter is greater than the first diameter, wherein the spacer includes a distally-facing ledge at a distalmost end of the first portion, and the introducer sheath contacts the ledge;

the lumen of the spacer is configured to be contiguous with the lumen of the biopsy gun when the spacer is connected to the biopsy gun; and the lumen of the spacer and the lumen of the introducer sheath are configured to accept the biopsy needle.

28. The biopsy system of claim 27, wherein the first diameter of the lumen of the spacer is constant from a proximal end of the first portion to the distalmost end of the first portion.

29. The biopsy system of claim 27, wherein the second diameter is greater than an outer diameter of the introducer sheath.

30. The biopsy system of claim 27, wherein a proximalmost end of the introducer sheath contacts the ledge.

31. The biopsy system of claim 27, wherein an outer surface of the introducer sheath contacts an inner wall of the spacer that defines the second diameter.

32. A method, comprising:

using the biopsy system of claim 27 by delivering the distal end of the introducer sheath into a body of a subject.

* * * * *